United States Patent [19]

Kyriacou

[11] 4,242,183

[45] Dec. 30, 1980

[54] HIGHLY ACTIVE SILVER CATHODE, PREPARATION OF SAME AND USE TO MAKE 2,3,5-TRICHLOROPYRIDINE

[75] Inventor: Demetrios Kyriacou, Clayton, Calif.

[73] Assignee: The Dow Chemical Company, Midland, Mich.

[21] Appl. No.: 29,600

[22] Filed: Apr. 13, 1979

[51] Int. Cl.³ .................. C25B 3/04; C25B 11/04; C25D 3/46; C07D 211/72

[52] U.S. Cl. .................. 204/73 R; 204/46 R; 204/290 R; 204/292; 546/345

[58] Field of Search ............ 546/345; 204/73 R, 292, 204/46 R, 290 R

[56] References Cited

U.S. PATENT DOCUMENTS

| | | | |
|---|---|---|---|
| 3,130,136 | 4/1964 | Wright | 204/72 |
| 3,449,162 | 6/1969 | Chand | 204/292 X |
| 3,479,276 | 11/1969 | Jung et al. | 204/290 R |
| 3,657,003 | 4/1972 | Kenney | 204/46 R X |
| 3,687,826 | 8/1972 | Seiber | 204/73 R |
| 3,694,332 | 9/1972 | Parker | 204/73 R |

OTHER PUBLICATIONS

Abramovitch, Pyridine and its Derivatives, Supp. Part II, 446, 447, pub. by Interscience (1974).
Organic Chemistry by Brewster, pp. 493 and 494, pub. by Prentice-Hall (1948).
Roberts et al., Chem. Comm. J. Chem. Soc. 1967, pp. 893, 894.
Klingsberg, Pyridine and Its Derivatives, Part II, pp. 345, 346, pub. by Interscience (1961).
Mao et al., J. Electrochem. Soc., vol. 117, pp. 1319-1323, 10-70.

*Primary Examiner*—F. Edmundson
*Attorney, Agent, or Firm*—Robert R. Stringham

[57] ABSTRACT

A highly active cathode, having utility for electrolytic reduction of 2,3,5,6-tetrachloropyridine to 2,3,5-trichloropyridine, comprises a wet, immobilized layer of aggregated silver microcrystals, formed by the electrolytic reduction of colloidal, silver oxide particles in the presence of water and hydroxyl ions.

13 Claims, No Drawings

4,242,183

HIGHLY ACTIVE SILVER CATHODE, PREPARATION OF SAME AND USE TO MAKE 2,3,5-TRICHLOROPYRIDINE

BACKGROUND OF THE INVENTION

The electrolytic reduction of chloropyridines with cathodes other than silver and the use of silver cathodes for electrolytic reductions of other types of compounds are known. The electrochemical activities of different varieties of silver electrodes have been the subject of several academic studies.

U.S. Pat. No. 3,694,332 discloses the use of a lead or mercury cathode for the electrolytic reduction of pentachloropyridine to symmetrical (2,3,5,6-) tetrachloro pyridine. The reaction is carried out in a solution of a neutral or acidic salt and water in an organic solvent. Some over-reduction of the tetrachloropyridine to an unidentified trichloro pyridine is indicated to occur if the reduction is continued until complete conversion of the penatachloropyridine is attained. However, environmental considerations now weigh against the use of mercury and lead in commercial processes and lead cathodes are not highly efficient for the reduction. Furthermore, efforts to extend the method of the patent to the preparation of products comprising substantial proportions of any trichloropyridines have been unsuccessful, not only with lead and mercury cathodes but also with other cathodes designated in the patent as suitable. (Several of the latter cathodes have hydrogen overvoltages as low or lower than silver.)

U.S. Pat. No. 3,010,966 discloses the use of a silver sheet as a cathode in the electrolytic cleavage of bis(4-hydroxymethyl-5-hydroxy-6-methyl-pyridyl-(3)-methyl)-disulfide dihydrochloride-hydrate to 3-mercaptomethyl-4-hydroxymethyl-5-hydroxy-6-methylpyridine. The reduction is carried out in 1:2 c.HCl/H$_2$O.

Current efficiencies for the electrolytic reduction of 2-butyne-1,4-diol, at silver cathodes of several different types were examined by Kato and Sakuma; *J. Electrochem. Soc. Japan*, Overseas Ed. 27, 236–9 (1959); C.A. 58 12,171e. White silver and bright silver cathodes gave poor efficiencies but compressed powdered silver cathodes had efficiencies of about 80%.

A correlation between hydrogen overvoltage and ease of reduction of several different substrates for different cathode metals was attempted by A. T. Petrenko; *Electrokhimiya*, 3(2), 252–5 (1957; in Russian) C.A. 66 121,518w. In the case of silver and copper, a parallelism between hydrogen overvoltage and effectiveness for the reduction of glyceraldehyde was not found (in contrast to a "perfect parallelism" for tin, lead and cadmium). The abstract does not indicate that data was obtained for reduction of chlorocarbons.

The effectiveness, for oxygen reduction, of several porous silver electrodes, prepared by leaching of pressed mixtures of silver powder and ammonium bicarbonate, has been examined by Burshtein et al.; *Topl. Elem.*, 1968, 306–22 (in Russian), C.A. 73, 94,136f. The use of such porous silver electrodes—activated by inclusion of 2% of magnesium in a surface layer of the silver (on a carbonyl nickel layer)—for reduction of oxygen in 7 N KOH (at 90° C.) was also investigated by the author; *Electrokhimiya*, 1970, 6(7), 939–48 (in Russian), C.A. 73 94,035x.

Utilization of frequent polarity reversals in the electrolytic deposition of trace amounts of noble metals (such as silver) in or below the surfaces of substrate metals (such as nickel or tantalum) is disclosed in U.S. Pat. No. 3,645,860, which is directed to the preparation of electrocatalysts. The noble metal source solutions are extremely dilute and the amount of the incorporated metal is far less than that which would be equivalent to even a monatomic layer.

Periodic polarity reversals of substantial relative duration are resorted to in the process for electroplating silver (from basic cyanide solution) onto substrate metals, disclosed in U.S. Pat. No. 2,678,909. In this case, the result of the polarity reversals is said to be smoothing (i.e., a decrease in surface area) of the plated metal.

The activation of metals, for use as electrocatalysts, be repeated polarity reversals is generally disclosed in *Modern Electrochemistry*; Bockris and Reddy; Vol. 2, page 1170; Plenum Press, N.Y., 4th Ed., 1973.

No art more pertinent to the present invention than the foregoing is known of and it thus does not appear that silver electrodes (cathodes) of the character required for the efficient electrolytic reduction of 2,3,5,6-tetrachloropyridine to 2,3,5-trichloropyridine are disclosed or made obvious by the known art. The latter compound is a convenient and economic intermediate for the preparation of 3,5-dichloropyridyl-2-oxy-phenoxy-substituted carboxylic acids (see U.S. Pat. No. 4,140,520, for example)—which are highly active herbicides. Pentachloropyridine is now a readily prepared starting material, so it is apparent that an efficient method of producing 2,3,5-trichloropyridine from pentachloropyridine is to be desired.

OBJECTS OF THE INVENTION

A primary object of the present invention is to provide an improved silver electrode.

A corollary object is to provide such an electrode having particular utility as a cathode for the electrolytic replacement, by hydrogen, of an alpha chloro-substituent in 2,3,5,6-tetrachloropyridine.

A further object is to provide a process for the electrolytic reduction of polychloropyridines which does not require the use of environmentally-objectionable electrode materials.

Another object is to provide an efficient method of producing 2,3,5,6-tetrachloropyridine and/or 2,3,5-trichloropyridine from pentachloropyridine.

An additional object is to provide a simple, reliable method of converting conventional types of silver electrodes to cathodes having a superior activity/selectivity balance.

Yet another object is to provide a method of electrolytically reducing pentachloropyridine which requires considerably less energy than the known electrolytic method.

It is also an object to provide an activated cathode which utilizes silver microcrystals aggregated in the form of either a powder or as an adherent surface layer, and which can be reactivated in place.

Still other objects will be made apparent, to those versed in the art, by the following specifications and claims.

SUMMARY OF THE INVENTION

The article of the present invention is an electrode comprising a shaped electrical conductor in intimate contact with a water and hydroxyl ion-containing, immobilized, metastable layer of aggregated silver microcrystals formed by electrolytic reduction of colloidal, hydrous silver oxide particles in the presence of water and hydroxyl ions.

The metastable silver layer in the electrode of the invention may be further characterized as rendering the electrode highly active as a cathode for the electrolytic reduction of 2,3,5,6-tetrachloropyridine to 2,3,5-trichloropyridine. The essential physical-chemical nature of this layer depends on the continued inclusion of hydrated hydroxyl ions within it.

In one embodiment of the invention, the active silver layer is a body of silver powder constrained within a liquid permeable bag or envelope and the electrical conductor either is surrounded (at least partially) by the powder or constitutes the envelope which "surrounds" (contains) the powder. In this embodiment, the microcrystals pack together to form the powder particles.

In another embodiment, the active layer is adhered to a surface of the electrical conductor, the conductor preferably consisting of or being clad with silver. In this embodiment, the microscopic topography of the active surface layer can vary (according to the detailed manner in which the oxide particles were formed and reduced). For example, the silver microcrystals may aggregate by packing closely together to form a plurality of mono- and polypartite "bumps" or dendrites protruding from and contiguous with a surface portion of the conductor or, pack loosely to form discrete particles which cohere with each other and adhere to the surface as a porous or "spongy" blanket which conforms to the substrate topography.

When cathodically polarized, the foregoing electrode constitutes a more preferred embodiment of the present invention.

In a particularly preferred embodiment, at least a portion of the cathodically polarized electrode is immersed in a catholyte which comprises water and hydroxyl ions, and is contained in a cell otherwise adapted for carrying out electrolytic reductions.

The process for preparing the above-defined electrode is also within the ambit of the invention and comprises: p1 a. immersing an electrical conductor in a catholyte comprising water and hydroxyl ions, b. introducing to or forming in said catholyte colloidal, hydrous silver oxide particles, c. cathodically polarizing said conductor and electrolytically reducing said silver oxide particles, thereby forming aggregated silver microcrystals in contact with a surface of said conductor.

The silver oxide particles can be formed in the immediate vicinity of the conductor, as by anodizing a silver conductor, or may be formed elsewhere and transported to the conductor in the catholyte, as by stirring it.

In another process aspect, the invention is the use of the foregoing electrode to reduce 2,3,5,6-tetrachloropyridine to 2,3,5-trichloropyridine. The tetrachloropyridine may be provided as such or generated in situ by reduction of pentachloropyridine, and the reduction may be continued, without experiencing substantial overreduction, at least until the amounts of the tetrachloro- and trichloropyridine present in the catholyte are about equal.

DETAILED DESCRIPTION

The most critical features of the invention are (1) the active silver overlayer of the electrode must be composed of microcrystals formed by the electrolytic reduction of colloidal, hydrous, silver oxide particles, in contact with a solution comprising water and hydroxyl ions, and (2) the overlayer must be kept wet with water containing hydroxyl ions.

When the electrode is to take the form of a confined, liquid-permeable body of silver powder in contact with the electrical conductor, the initially formed silver particles in direct contact with the conductor function as part of the conductor for the formation of the next layer of particles, and so on. Similarly, contact between the conductor and the powder particles distal from it is by electrical conduction through the intervening portion of the powder body.

If at least the portion of the conductor surface which is to be immersed in the silver oxide dispersion (or in a catholyte) is defined by an outer layer of silver, the oxide to be reduced in activating (or reactivating) the electrode may be generated in situ by anodization of the silver. Thus, monolithic silver or silver-clad composite conductors are particularly convenient in affording electrodes which can be activated or reactivated in place in the cell to be used for carrying out a reduction.

Accordingly, silver or silver-clad conductors are preferred. The latter types of electrodes may be of any configuration—such as a screen, plate, rod, etc., which is suitable for their intended function and which permits ready access of liquid to the silver surface at which the oxide reduction must proceed.

The presence of noble metals other than silver in the active surface layer has not been found beneficial and base metals (nickel and copper, most notably) are definitely detrimental. Accordingly, it is highly desirable to minimize the content of metal ions other than silver in the reduction medium around the conductor (or electrode).

It then follows that the conductor either should not be subjected to anodization or should consist of silver or a material which will not provide any substantial amount of ions (or reducible oxidation products) of other metals under the contemplated anodization conditions. (Analytically pure silver is not required but is of course preferred.)

The outer (or substrate) silver layer in a composite conductor comprising the same may be formed in any suitable manner, such as, for example, by electroplating silver on an electroconductive "core" or underbody. Since it is desirable for this layer to have a high surface area, the underbody surface on which the silver layer is formed does not have to be—and preferably is not—smooth. Similarly, a method of depositing the outer layer which favors columnar or dendritic growth or otherwise results in a high surface area—but not in lateral discontinuities in the silver in immediate contact with the underbody—is preferred.

In one embodiment of the invention, the type of active overlayer which consists of protrusions contiguous with the silver substrate layer may in turn serve as a once-removed substrate layer which can be induced, by periodic polarity reversals, to cover itself with a comforming, porous blanket of cohered silver particles, thereby providing an outermost portion of the overlayer which has a still higher surface area structure of a character more like that of a "molecular sieve".

If the conductor is not to be subjected to anodization, it may consist of any otherwise inert, electroconductive material to which the silver microcrystals (as such or as particulate aggregates thereof) will adhere sufficiently well not to be swept off by a stirred catholyte. This includes nickel, stainless steel and—at least in principle—copper and graphite. Similarly, if such a conductor is first clad with a substantial thickness of silver, it then becomes a composite conductor which may be activated by anodization.

As noted above, the colloidal silver oxide particles can be preformed and then introduced to the catholyte or can be formed in the catholyte—optionally, in the layer of catholyte in immediate contact with the silver base layer.

A convenient method of forming the oxide in a catholyte comprising water and hydroxyl ions is simply to add a small amount of a water-soluble silver salt, such as silver nitrate, with sufficient agitation to keep the resultant colloidal, hydrous, silver oxide particles well dispersed. Preferably, the salt is added as a dilute solution in water. Once formed, the oxide particles contact and are reduced at the negatively-charged cathode surface (the surface of the conductor) to build up the microcrystalline silver overlayer, i.e., to activate the cathode.

Formation of an active overlayer consisting of a non-adhered silver powder is facilitated by effectively immobilizing the silver oxide particles (to be reduced) in close contact with each other and/or the conductor; the reduction then more closely approximates an all-at-once production of the microcrystals and growth of earlier formed nuclei (crystals) by accretion of later formed silver is minimized.

The envelope may or may not be electroconductive, but must be readily permeable to both phases of the catholyte. If it is conductive, it may also function as the conductor. If it is not, a separate shaped conductive member (such as a wire or patch of metal screening, for example) which can be inserted or embedded in the body of oxide particles to be reduced, will be required. The envelope may be foraminous (as a fine meshed gauze or screen, for example) or microporous (as a TEFLON ® or polyethylene diaphragm having a porosity and averge pore size such as to permit a practical rate of transport through it of an emulsion of the water, base, solvent and reducible material, for example).

The envelope should be so formed about the body of silver oxide particles (to be reduced), as by flattening, crimping or stretching, as to exert some compression on it, thereby ensuring better contact between the resultant silver powder particles.

If further activation (or reactivation) of the powder, by anodization, is not contemplated, the central conductor or conductive envelope can consist of a metal such as nickel, stainless steel or even copper, to which silver has less tendency to adhere, thereby further ensuring a high conversion of the silver oxide particles to unattached silver particles.

In an alternative method of activation ("anodization") the silver which makes up the active overlayer is derived from the (silver) substrate layer itself. The unactivated electrode is dipped or immersed in a catholyte containing water and hydroxyl ions and is anodized (anodically polarized), thereby converting some of the silver in the base layer surface to colloidal silver oxide and roughening (corroding) the surface at the same time. The polarity of the electrode is then reversed and the oxide electrolytically converted to protrusions or particles of microcrystalline silver (without re-smoothing the surface it is adhered to). Preferably, the polarity reversal is repeated several times at intervals of about 30 seconds. This same procedure can also be employed to reactivate a cathode of the invention which exhibits diminished activity.

Water plays an important, albeit not well understood, role in the formation and retention of the fine structure which is essential to the activity (and selectivity) of the metastable silver overlayer. Both water and hydroxyl ions (hydrated hydroxide ions, at least) must be included in the overlayer when it is formed—and when it is utilized in a cathode. Once formed, the microcrystalline superstructure will collapse somewhat and its activity will be at least substantially diminished if its content of water is allowed to decrease below some minimum critical level. Whether or not this level corresponds to a monomolecular layer (over the entire fluid-accessible surface of the overlayer) is not known. Although the critical contents of water and base can readily be determined for any specific, reproducible cathode, this is not necessary if the cathode is simply kept immersed in an appropriate basic, aqueous medium. Preferably, the latter medium is simply that in which the electrode was immersed when it was "activated", or is the aqueous phase of the catholyte which will be employed for a contemplated reduction.

The activation procedure is not adversely effected by the presence, with the required basic, aqueous medium employed, of an organic phase comprising the material to be reduced (such as pentachloropyridine, for example) and the organic solvent for the same. Accordingly, activation most conveniently is carried out simply as the first step in the reduction for which the cathode is employed. This is true for either of the two general activation methods discussed above, which will now be discussed in more detail.

In the activation method involving formation of the silver oxide particles in the catholyte, it is not necessary to establish a substantial silver content in the (aqueous phase of the) catholyte; silver contents of about 100 ppm (parts per million) are generally sufficient and contents substantially in excess of about 500 ppm are of no additional benefit and may actually be wasteful. The solution of the silver salt can be added to a preformed catholyte mixture or to the aqueous base component thereof before the latter is dispersed with the organic phase. The requisite degree of agitation during the oxide deposition step is conveniently attained with magnetic stirring.

The silver oxide particles to be reduced in forming an active silver overlayer may be preformed in a separate container and then introduced to the catholyte—together with or separated from the aqueous medium in which they were formed. When the overlayer is to take the form of a silver powder, it is convenient to filter out the oxide particles and to transfer them (wet with aqueous base) to the envelope in which they will be reduced. The envelope can be formed from a flat sheet of gauze or other suitable material on which the oxide particles have been placed, or may be a preformed, porous container (such as a porous fluorocarbon elastomer bag, for example) in which the particles are lightly packed.

In the activation method involving anodization of the electrode, the current density is usually controlled so that the potential at the electrode surface rises, in a period of several minutes, from an initial value of, say, zero volts to a final value of at least $+0.3$ volts and preferably about $+0.6$ volts. It is not necessary to add any silver to the catholyte (or aqueous base) in this method.

It is known (*Electrochemical Reactions*, Charlot et al.; pp. 298, 9; Elsevier Pub. Co., Amsterdam, N.Y., 1962)

that the electrolytic oxidation of silver at progressively higher potentials, in the presence of hydroxyl ions, results in the formation of not only Aq₂O but also of higher oxides in which silver takes on nominal valences greater than one. The calculated positive (anode) potentials corresponding to formation of $Aq_2O_2$ and $Aq_2O_3$, in about 13 N KOH, are, respectively, about +0.6 and about +0.8 volts. A potential of about +0.6 volts is currently regarded as optimum for the in-situ preparation of silver oxide particles from which the active silver layer is to be prepared; however, potentials as high as +0.8 volts are not ruled out.

Reduction of the oxide deposit requires negative polarization of the cathode in both methods of activation. In the first method discussed above, the cathode potential is negative to start with and may range from about −0.5 to about −2.0 volts; preferably it is from about −1.0 to about −1.5 volts. In the second method, the polarization of the cathode is gradually reversed. That is, the cathode potential is gradually reduced from the value (about +0.3 to about +0.6 volts) attained in the oxidation step, to a value of about −0.5 volts or less (down to about −2.0 volts). In the first method, the current is relatively low in the early stage of oxide reduction. Thereafter, the current will rise to an essentially steady value, assuming a reducible material is present in the catholyte. However, in the second method, the current drops off from an initially higher level to a minimum, at which point (potential about −0.5 volts) the oxide reduction is complete. If the potential is lowered further, the current will then increase—again assuming a reducible material is present—to a value of about 1.5 amps (cathode potential about −1.3 to about −1.5 volts).

Before the cathode is activated by either method, it preferably is cleaned, as by immersing it in aqueous hydrochloric acid (1:1 water and c.HCl) for about ten minutes. Similarly, when a cathode which has been used as such for some time and is to be reactivated, it should first be cleaned in the same manner, to essentially remove any detrimental metals which may have plated out on it.

Suitable catholytes for carrying out electrolytic reductions with cathodes of the present invention comprise water, a water-soluble hydroxide-ion source material, the reducible material and a solvent for the latter material.

The water-soluble base (hydroxide-ion source material) can be a hydroxide—an alkali metal hydroxide, for example—or a salt—such as sodium acetate, for example—of a strong base and a weak acid. Other types of water soluble bases—such as ammonia or triethanolamine, for example—may also be used as hydroxide-ion source materials, provided that the amount of the latter type of base employed is not such as to interfere (by complexing with silver ions) with such reactivation of the cathode as may become necessary.

The solvent component of the catholyte preferably is an inert organic liquid which is water-miscible and is able to dissolve at least enough of the reducible material to enable the reduction to proceed at a useful rate. By "inert" is meant that the solvent does not detrimentally alter or react (with the cathode or catholyte materials) to an intolerable extent, under the conditions employed for the reduction. Generally exemplary of such solvents are THF (tetrahydrofuran), dioxane, alcohols, lower alkylene (and dialkylene) glycol monoethers and diethers, solfolane and lower amides—such as dimethylformamide (DMF) or dimethyl acetamide. THF and glycol ether/isopropanol mixtures are preferred solvents for the reduction of pentachloro- and/or 2,3,5,6-tetrachloropyridine.

The relative amounts and compositions of the aqueous and organic phases of the catholyte can vary widely. The content of hydroxyl ion in the aqueous phase should be such as to provide a pH which is greater than 7 but is not so high that attack of hydroxyl on the reducible material proceeds to any substantial extent. The content of the reducible material in the organic phase should be as high as can be attained without rendering that phase incapable of containing at least a few percent of dissolved water. The most appropriate relative amounts of the catholyte ingredients for any particular reduction of course can readily be determined empirically.

Conventional anodes are suitable for use with the cathodes of the present invention in carrying out electrolytic reductions. Thus, the anode may consist of any otherwise suitable material, such as graphite, platinum or silver, for example, which does not deleteriously interact with the anolyte.

Suitable anolytes comprise water and at least an amount of hydroxyl ion sufficient to suppress undesired anodic oxidations of other oxidizeable anions as may be present in them. Ordinarily, the anolyte will be a single aqueous phase and will not include organic materials. Substantial intermixing of the anolyte and catholyte is prevented by use of a porous barrier means, such as a conventional porous ceramic anolyte cup or an intervening porous diaphragm, for example. Solutions of alkali metal hydroxides in water are generally suitable anolytes and 25% aqueous sodium hydroxide has been found highly satisfactory for the reduction of pentachloropyridine or 2,3,5,6-tetrachloropyridine.

The cathode potential and the cell voltage employed will vary with the natures of the reducible material and the base used, the cell geometry, and so on. However, a cathode potential of about −1 to about −1.5 volts (relative to a saturated calomel electrode) and a cell voltage of about 7–9 volts are preferred for the reduction of pentachloropyridine or 2,3,5,6-tetrachloropyridine. It is noteworthy that good conversions of the tetrachloropyridine to 2,3,5-trichloropyridine can be attained at a cathode potential of about −1.3 volts and a cell voltage of about 8 volts (using a porous ceramic cup to separate the catholyte and anolyte).

Suitable ranges for the other parameters of the latter reductions are:

Current density, about 0.05 to about 0.5 amps/in²; (preferably about 0.2 to about 0.3 amps/in²).

Temperature, about 10 to about 50° C.; (preferably about 20° to about 35° C.).

Contact time*, about 2.5 hours for essentially complete conversion of pentachloropyridine to 2,3,5,6-tetrachloropyridine and about 6 hours total for essentially complete conversion to a product containing about equal proportions of the tetra- and 2,3,5-trichloropyridines, and a small amount of dichloropyridine(s).

* Cathode not reactivated during the reduction.

Electrode spacing, from about 1 to about 2.5 cm; larger distances increase the cell voltage required and smaller distances are more likely to result in contact of one of the electrodes with the intervening, porous, anolyte container, thereby hindering circulation of the liquid (catholyte or anolyte) surrounding that electrode.

The following examples are for purposes of illustration and are not to be construed as limiting the present invention in a manner inconsistent with the claims appended to these specifications.

EXAMPLES

1. In situ activation of silver screen cathode and reduction of pentachloropyridine to a mixture of 2,3,5,6-tetrachloropyridine and 2,3,5-trichloropyridine.

To a 200 ml beaker containing a magnetic stirring bar is charged 100 ml of a 1:1 solution of THF and water, 10 grams of pentachloropyridine and 15 grams of sodium acetate. A porous ceramic (alundum) anolyte cup about 5 cm tall and 5 cm in diameter is positioned so that it is immersed to a depth of about 4 cm in the resulting two-phase mixture. 50 ml of 25% aqueous sodium hydroxide is charged to the cup and a silver screen anode, shaped as a cylinder about 4 cm tall and 3 cm in diameter, is stood on end in the cup, the cylinder and cup axes coinciding. A silver screen cathode, shaped as a cylinder about 7 cm in diameter and about 4 cm tall, is positioned concentrically around the anode cup and fully immersed in the catholyte. A saturated calomel reference electrode is immersed in the catholyte outside the cathode, with its tip almost touching the cathode. A water bath is provided to control the temperature in the cell at about 20°–30° C. A source of variable D.C. power, a switching means and means for measuring the cell voltage, the cathode voltage (relative to the reference electode) and the cell current, are appropriately hooked up with the cell.

The magnetic stirrer is turned on and set at a rate which provides sufficiently intense mixing of the catholyte phases to, in effect, form an emulsion. The D.C. circuit is closed and the cathode potential, relative to the reference electrode, is set at about −1.5 volts. The potential difference across the cell is adjusted to a value (∼8 volts) such that the cell current is about 1.0 amperes. As soon as the current starts to flow, one ml of a 2% solution of silver nitrate in water is added. Over a period of about 30 seconds, the current tends to rise, to an extent that the cathode potential must be cut back to about −1.1 volts (thereby reducing the cell voltage also by about 0.4 volt) in order to restore the cell current to ∼1.0 amps. That is, the cathode has now been activated.

The reduction is allowed to proceed at a rate of about 1.0 amperes (current density ∼0.5 amps/in$^2$) and samples of the catholyte are periodically withdrawn for analysis by vapor phase chromatography and infrared spectrometry (vis-a-vis authentic standard samples of the starting material and the anticipated reduction products). The approximate relative amounts of the charged pentachloropyridine reporting in the product as such and as the tetra- and trichloro derivatives are given for successive samples in Table 1 below.

TABLE 1

| Total Elapsed Time Hours | % Pentachloropyridine Reporting as: | | |
|---|---|---|---|
| | Penta- | 2,3,5,6-tetra | 2,3,5-tri- |
| 0.5 | 59 | 41 | 0 |
| 1.0 | 38 | 62 | 0 |
| 2.0 | 15 | 85− | Trace |
| 2.8 | 5 | 90 | 5 |
| 3.0 | 4+ | 90− | |

TABLE 1-continued

| Total Elapsed Time Hours | % Pentachloropyridine Reporting as: | | |
|---|---|---|---|
| | Penta- | 2,3,5,6-tetra | 2,3,5-tri- |
| 4.0 | Trace | 85− | 15 |
| 5.0 | 0 | 70 | 30 |
| 6.0 | 0 | 50 | 50 |

The product is extracted from the catholyte with three 20 ml portions of dichloromethane and the combined extracts are washed with water and "stripped" by evaporation—precautions being taken to avoid losses of the trichloro compound by sublimation. The resulting residium is a mixture of crystalline solids and a little oil, total weight about 9.5 grams. The 2,3,5-trichloropyridine component of the crystalline phase is separated by sublimation and the residual 2,3,5,6-tetrachloropyridine is purified by recrystallization or is utilized "as is" as a starting material for production of more of the trichloro- derivative (by electrolytic reduction in the preceding manner).

2. Essentially the same results are obtained when the preceding experiment is repeated with an anode which is graphite, steel or platinum/nickel and a catholyte in which the liquid components are as above or are water, benzene and isopropanol (or a glycol ether) in the approximate proportions (by volume) of 5.5/2.5/5.0.

3. Characterization of Activated Silver Electrodes of the Invention.

(a) A rectangular (0.005"×2"×3") piece of smooth silver foil is immersed in 10% aqueous caustic containing several hundred parts per million of colloidal silver oxide (formed upon addition of a dilute silver nitrate solution to the caustic). A counter electrode is also immersed in the caustic and the silver foil is cathodically polarized at a potential (relative to a saturated calomel electrode) of about −1.5 volts and the potential difference between it and the anode is adjusted to give a current of about 1.5 amperes. Reduction of silver oxide at the cathode surface is allowed to proceed for about half a minute.

A small portion of the silverized foil is cut off, air-dried and observed to have a rough matte white appearance. The remainder of the foil is kept immersed in the catholyte and is subjected (by means of a throw switch) to a series of four polarity reversals at thirty second intervals. The resulting "anodized" foil is removed from the cell, air-dried and found to have the appearance of dark brown to black foam.

Both portions of the foil (on the side facing the anode) are examined by scanning electron microscopy (SEM), X-ray dispersive fluorescence and electron diffraction (reflection). The outer layer of the matte white (unanodized) foil is "seen" to be a deposit of closely spaced, generally hemi-spherical "bumps" which are contiguous with the underlying foil, have maximum dimensions of up to about 25 microns and are composed of densely packed, face-centered, cubic silver microcrystals (about 0.05 to 1 micron in "diameter"), the bumps being laterally connected at their bases and in some instances "fused" together to form polypartite bumps having maximum dimensions of from about 30 to about 50 microns.

The microscopic topography of the anodized foil is essentially the same, but the bumps are coated with a relatively thin layer of a silver deposit having the appearance of a "moss" at 100 magnifications. The moss is found to consist of loosely packed, face-centered, cubic silver microcrystals having a narrow size distribution around an average maximum dimension of about 0.05 microns. At a magnification of 10,000X, the "moss" looks like sponge cake and may be described as having a "spongy" character.

(b) A silver layer is electroplated from an ammoniacal solution of silver nitrate on a nickel substrate, peeled off as a foil and sampled for examination by SEM, X-ray fluorescence and electron diffraction. The surface of the foil which has been exposed to the silver solution, washed and air dried, is matte-white in appearance and, at 2000 magnifications, is "seen" to have a surface layer of generally irregular, flattened "bumps" which have maximum dimensions of up to about 25 microns and are so embossed with flattened, irregularly shaped, microprotrusions as to have an eroded appearance. Some of the bumps consist of portions of well defined, individual crystallites having maximum dimensions of up to about 6-10 microns. At a magnification of 50,000X, all discrete surface areas are relatively smooth in appearance.

The remainder of the foil is anodized in the preceding manner (a, above), washed, air-dried and examined by SEM, etc. It has a brown color and is found to be coated with a layer of generally dendritic protrusions, of which the more elongate are joined at their bases into clusters—in some instances being largely fused together. The individual dendrites are seen (at 2000X) to have "diameters" of about 5-10 microns and lengths of about 10-20 microns. These dendrites are composed of closely packed, face-centered, cubic silver microcrystals and the dendrite surfaces are seen (at 50,000X) to be defined by an outermost, porous layer of discrete but cohered, generally spherical to oblate, silver crystallites varying in size (maximum dimension) from about 0.05 to 0.07 microns.

(c) A piece of clean silver foil, essentially the same as that employed in part (a) of this example, is examined by SEM and is "seen" to have a surface resembling (at 500X) that of a paper towel (at 1X). At 10,000X, this surface shows a pattern of grain boundaries resembling incipient cracks between slight elevations in an otherwise flat body of mud.

The foil is immersed in 6% aqueous NaOH in which a counter electrode is also immersed and is anodized, as follows, for 3 minutes. The potential of the foil (relative to a saturated calomel electrode) is raised from 0 to +0.3 volts in about 30 seconds and then, gradually, to +0.6 volts during the following 2.5 minutes. The potential is then gradually reduced to 0, and finally to −1.3 volts.

The anodized foil, together with enough of the cell liquor to keep it covered, is then sealed in a glass container and submitted for prompt examination by SEM, X-ray dispersive fluorescence and electron diffraction.

A sample of the wet, anodized foil is cut off, glued, wet, to an SEM stub and immediately placed in the SEM column for imaging. Another sample is cut off and allowed to air dry 24 hours before being scanned. The remainder of the anodized foil is allowed to age 24 hours in the cell liquor and then scanned.

The freshly activated (wet) foil sample is "seen", at 12,500X, to be covered with an adherent, highly porous blanket of cohered, angular particles consisting predominantly of more than one (face centered, cubic) silver microcrystal each and ranging in size (maximum dimension) from about 120Å (0.012 micron) to about 0.5 micron.

The structure of the blanket on the air-dried sample is found to be uniformly more condensed and to comprise a high proportion of relatively large (0.2-0.5 microns maximum dimension) particles readily recognized (at 25,000X) as generally cubical in shape.

The coating on the wet-aged foil sample is found to have condensed less uniformly, having pulled apart laterally in some places to expose underlying, essentially smooth surface areas. The proportion of generally cubical particles is lower and they are less well defined and, on the average, smaller (up to about 0.3 microns, maximum dimension).

4. Preparation of Silver Powder Cathode.

An amount of hydrous silver oxide(s) precipitate containing 2 grams of silver is formed by adding a dilute (2%) aqueous silver nitrate solution to a stirred body of 5% aqueous NaOH. The precipitate is filtered out and transferred (wet) to a flat, appropriately cut piece of 100 mesh, stainless steel screen, which is then folded and edge-crimped to form an electrically conductive, 5 cm × 7.5 cm envelope containing—and restraining—the oxide precipitate. The envelope is then immersed in 5% aqueous NaOH, in which a graphite counter electrode is also immersed, and cathodically polarized to reduce the oxide(s) to powdered silver. The current gradually drops off, over a period of 15 minutes, from an initial value of about 4 amperes to a then steady value of about 0.5 amperes (at an average cathode potential of about −1.5 volts), and the reduction is essentially complete.

A sample of the resulting silver powder is removed, together with some of the cell liquor, and submitted for immediate SEM (etc.) examination without being dried. The powder particles are found to be essentially the same as those making up the coating on the freshly activated, wet foil sample in part (c) of the preceding example.

The remainder of the powder is employed (with the envelope) as the cathode for several successive pentachloropyridine reductions over a period of 20 hours. No loss in activity is observed, the reductions being carried out in essentially the same manner and with essentially the same results as in Example 1 herein.

What is claimed is:

1. An electrode comprising a shaped electrical conductor in intimate contact with a water and hydroxyl ion-containing immobilized, metastable layer of aggregated silver microcrystals formed by electrolytic reduction of colloidal, hydrous silver oxide particles in the presence of water and hydroxyl ions.

2. An electrode as in claim 1 in which said silver layer is a body of silver powder constrained within a liquid permeable bag or envelope and the electrical conductor either is at least partially surrounded by the powder or constitutes said envelope.

3. An electrode as in claim 1 in which said silver layer is adhered to a surface of the conductor and is composed of aggregated silver microcrystals.

4. An electrode as in claim 3 in which said microcrystals are densely packed in the form of protrusions extending from and contiguous with the portion of the conductor defining said surface.

5. An electrode as in claim 4 wherein said portion of the conductor consists of silver.

6. An electrode as in claim 3 in which said microcrystals are aggregated as discrete but cohered particles.

7. An electrode as in claim 6 wherein the portion of said conductor defining said surface consists of silver.

8. An electrode as in claim 1 in which said conductor is a silver monolith or is at least partially clad with silver.

9. The method of preparing an electrode as defined in claim 1, said method comprising:
   a. immersing an electrical conductor in a catholyte comprising water and hydroxyl ions,
   b. introducing to or forming in said catholyte colloidal, hydrous, silver oxide particles,
   c. cathodically polarizing said conductor and electrolytically reducing said oxide particles, thereby forming aggregated silver microcrystals in contact with a surface of said conductor.

10. The method of claim 9 wherein said conductor is a silver monolith or is at least partly clad with metallic silver and said oxide particles are derived from that silver by anodically polarizing the conductor under a potential of up to about +0.8 volts, relative to a standard saturated calomel electrode.

11. The method of claim 10 in which said electrode is repeatedly alternated from cathodic to anodic and anodic to cathodic polarization, the cathode potential being in each instance within the range of from −0.5 to −2.0 volts, relative to a standard saturated calomel electrode.

12. The method of claim 9 wherein said oxide particles are formed by the reaction of silver nitrate with an alkali metal hydroxide in water.

13. The process for preparing 2,3,5-trichloropyridine which comprises electrolytically reducing 2,3,5,6-tetrachloropyridine at an electrode as defined in claim 1, said catholyte including an organic solvent for said tetrachloropyridine.

* * * * *

UNITED STATES PATENT AND TRADEMARK OFFICE
CERTIFICATE OF CORRECTION

PATENT NO. : 4,242,183

DATED : December 30, 1980

INVENTOR(S) : Demetrios Kyriacou

It is certified that error appears in the above—identified patent and that said Letters Patent is hereby corrected as shown below:

Column 3, line 41, after the colon "pl" should be deleted;

Column 7, line 68, "sulfolane" has been misspelled;

Column 9, Table 1, in the column "2,3,5-tri-" the last number in the column should be -- 6 --.

Signed and Sealed this

Twenty-first Day of July 1981

[SEAL]

Attest:

GERALD J. MOSSINGHOFF

Attesting Officer      Commissioner of Patents and Trademarks